(12) United States Patent
Houfburg

(10) Patent No.: US 7,037,339 B2
(45) Date of Patent: May 2, 2006

(54) MODULAR SPINAL FUSION DEVICE

(75) Inventor: Rodney L. Houfburg, Prior Lake, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 207 days.

(21) Appl. No.: 10/261,081

(22) Filed: Sep. 27, 2002

(65) Prior Publication Data

US 2003/0078661 A1    Apr. 24, 2003

Related U.S. Application Data

(60) Provisional application No. 60/368,950, filed on Mar. 29, 2002, provisional application No. 60/325,585, filed on Sep. 27, 2001.

(51) Int. Cl.
*A61F 2/44* (2006.01)

(52) U.S. Cl. .................................. 623/17.11

(58) Field of Classification Search ............ 623/11.11, 623/16.11, 17.11, 17.16, 23.5, 23.51, 23.56, 623/23.57, 23.58, 23.59, 23.6, 23.61, 23.63; 606/60, 61
See application file for complete search history.

(56) References Cited

U.S. PATENT DOCUMENTS

| 748,603 A * | 1/1904 | Henry ........................ 52/590.1 |
|---|---|---|
| 3,562,988 A * | 2/1971 | Gregiore ........................ 52/279 |
| 5,112,354 A | 5/1992 | Sires |
| 5,192,327 A * | 3/1993 | Brantigan ..................... 623/17 |
| 5,298,254 A | 3/1994 | Prewett et al. |
| 5,306,302 A | 4/1994 | Bauer et al. |
| 5,514,180 A | 5/1996 | Heggeness et al. |
| 5,653,621 A * | 8/1997 | Yao ............................ 446/127 |
| 5,728,159 A | 3/1998 | Stroever et al. |
| 5,893,890 A | 4/1999 | Pisharodi |
| 5,899,939 A | 5/1999 | Boyce et al. |
| 5,972,368 A | 10/1999 | McKay |
| 6,025,538 A | 2/2000 | Yaccarino, III |
| 6,033,438 A | 3/2000 | Bianchi et al. |
| 6,096,080 A | 8/2000 | Nicholson et al. |
| 6,159,211 A | 12/2000 | Boriani et al. |
| 6,159,244 A * | 12/2000 | Suddaby .................. 623/17.11 |
| 6,174,311 B1 | 1/2001 | Branch et al. |
| 6,193,757 B1 | 2/2001 | Foley et al. |

(Continued)

FOREIGN PATENT DOCUMENTS

DE                19710392 C1 *   7/1999

(Continued)

*Primary Examiner*—Eduardo C. Robert
*Assistant Examiner*—Anu Ramana
(74) *Attorney, Agent, or Firm*—Faegre & Benson LLP

(57) ABSTRACT

An implant is disclosed for use in stabilization of one or more bones, for example, adjacent vertebrae. The implant includes two or more coupled structural elements. Each structural element includes a first end spaced apart by a side surface from a second end. The side surfaces of each structural element include at least one recess and the structural elements are coupled by matingly engaging one or more recesses.

26 Claims, 17 Drawing Sheets

U.S. PATENT DOCUMENTS

| | | | |
|---|---|---|---|
| 6,224,631 B1 * | 5/2001 | Kohrs | 623/17.11 |
| 6,258,125 B1 * | 7/2001 | Paul et al. | 623/17.11 |
| 6,270,528 B1 | 8/2001 | McKay | |
| 6,364,880 B1 * | 4/2002 | Michelson | 606/61 |
| 6,387,130 B1 * | 5/2002 | Stone et al. | 623/17.16 |
| 6,419,705 B1 * | 7/2002 | Erickson | 623/17.16 |
| 6,468,311 B1 | 10/2002 | Boyd et al. | |
| 6,500,205 B1 * | 12/2002 | Michelson | 623/17.16 |
| 6,558,424 B1 * | 5/2003 | Thalgott | 623/17.16 |
| 6,824,565 B1 * | 11/2004 | Muhanna et al. | 623/17.16 |
| 2001/0031254 A1 | 10/2001 | Bianchi et al. | |
| 2002/0045904 A1 * | 4/2002 | Fuss et al. | 606/99 |
| 2002/0082693 A1 * | 6/2002 | Ahlgren | 623/17.11 |
| 2002/0106393 A1 | 8/2002 | Bianchi et al. | |

FOREIGN PATENT DOCUMENTS

| | | |
|---|---|---|
| WO | WO 98/17209 | 4/1998 |
| WO | WO 99/09914 | 3/1999 |
| WO | WO 00/24327 | 5/2000 |
| WO | WO 00/41654 | 7/2000 |
| WO | WO 00/74608 A1 | 12/2000 |
| WO | WO 01/70137 A2 | 9/2001 |

* cited by examiner

FIG. 1B
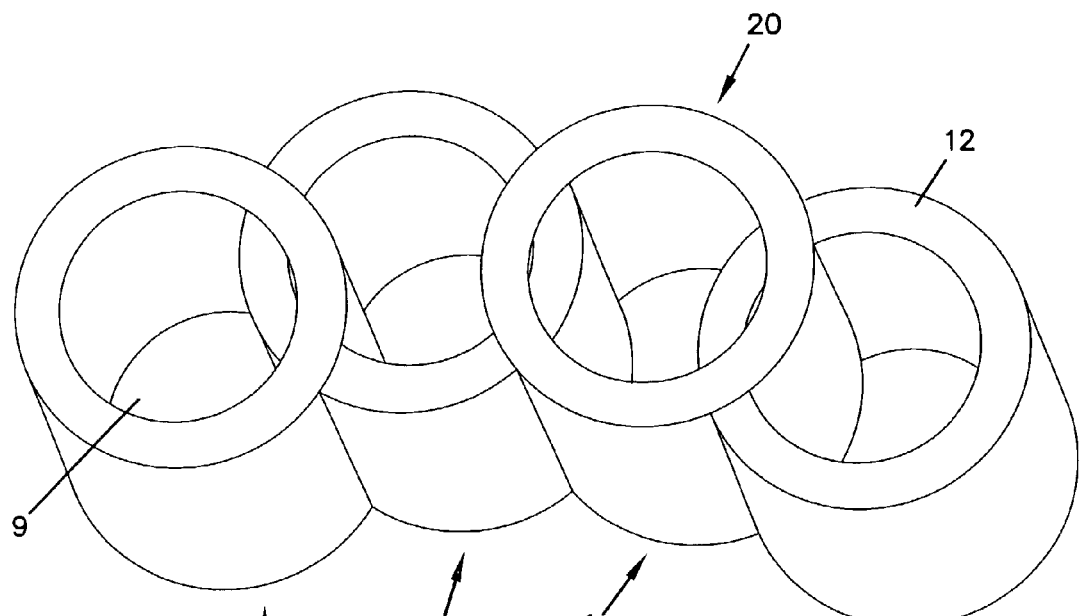
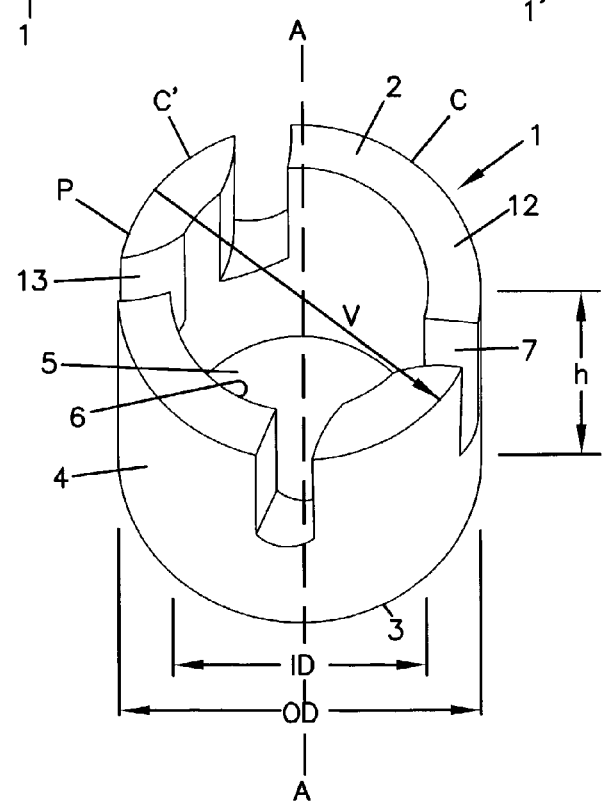
FIG. 1A

FIG. 4B
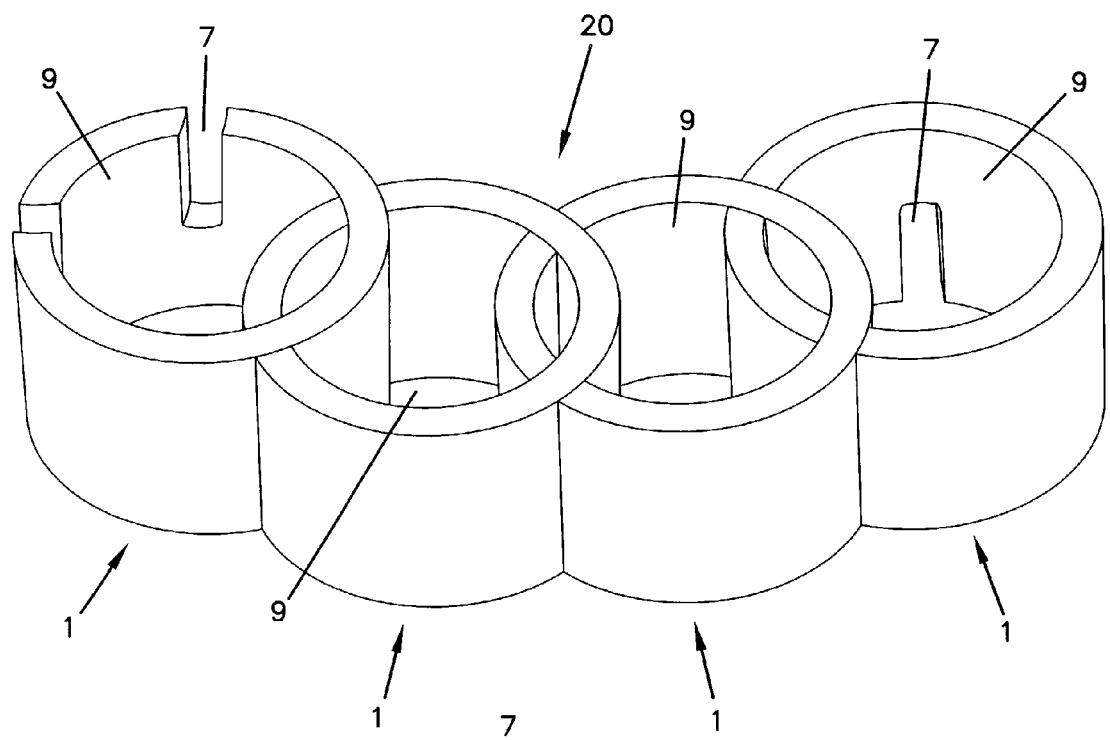
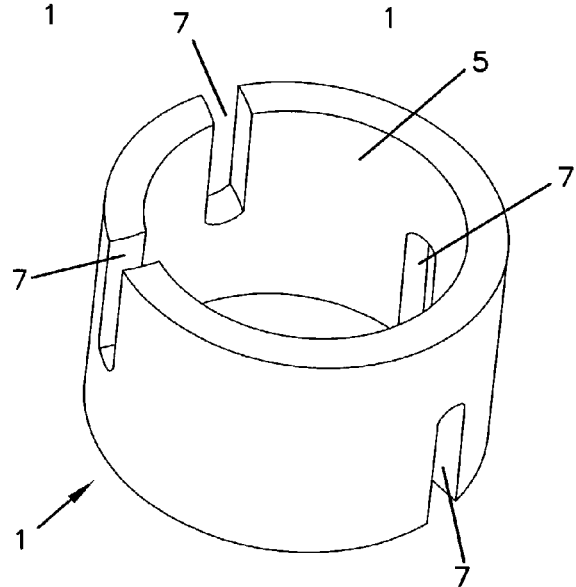
FIG. 4A

FIG. 6
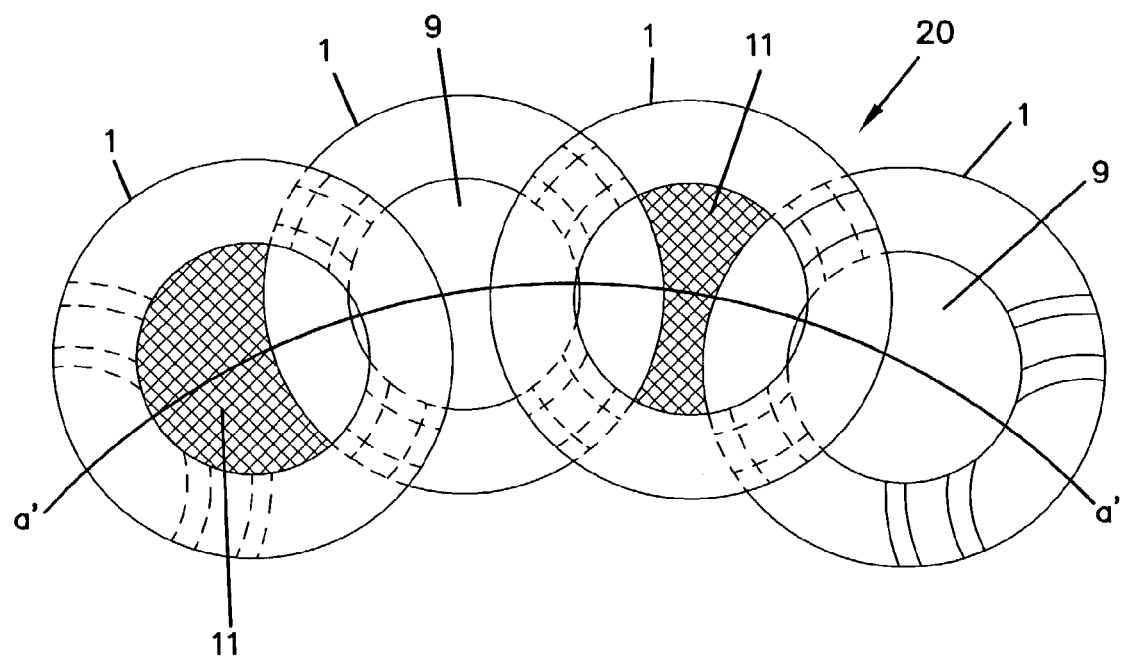
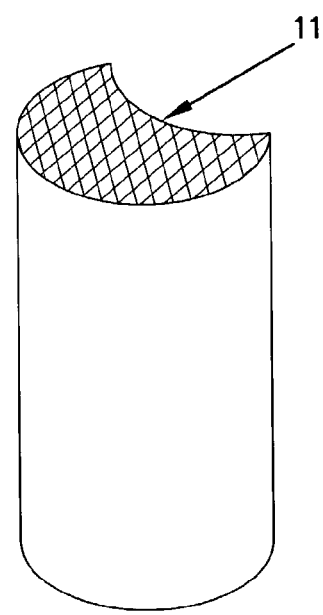
FIG. 7

FIG. 12
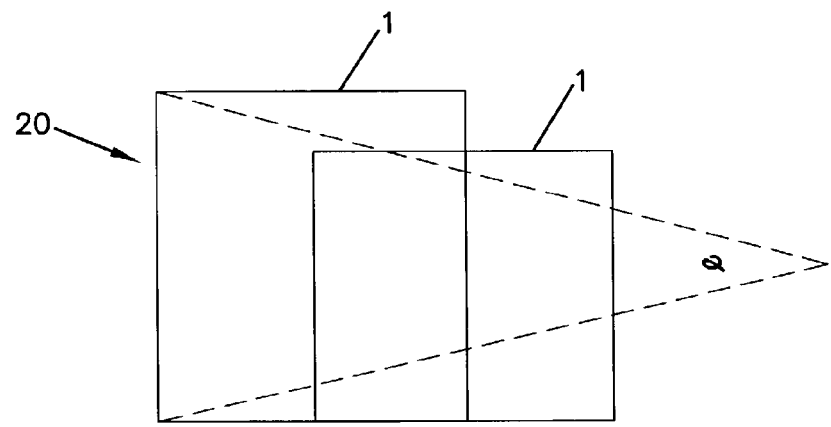
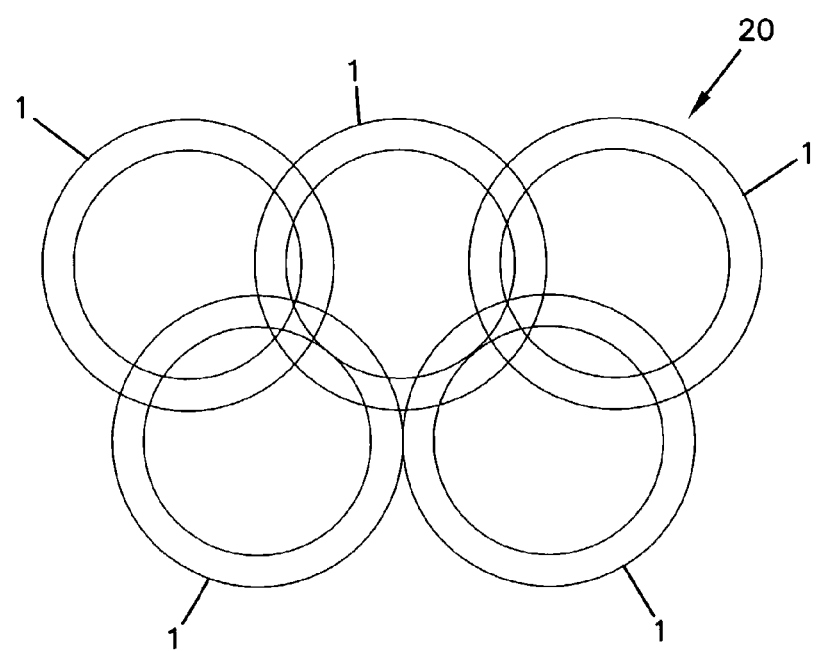
FIG. 8

FIG. 11
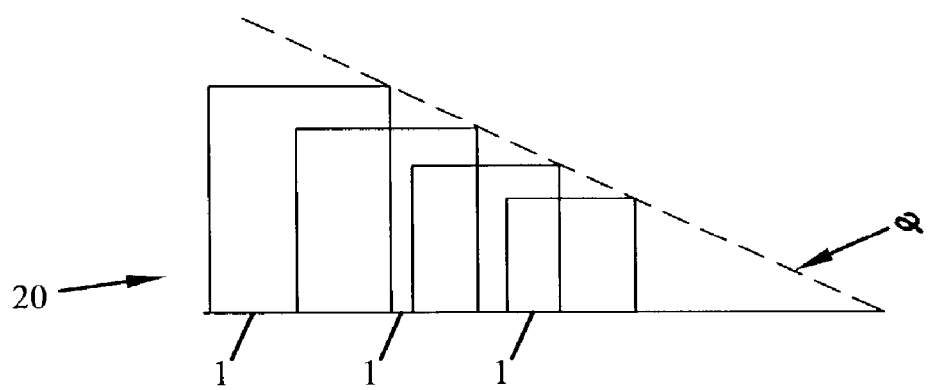
FIG. 9
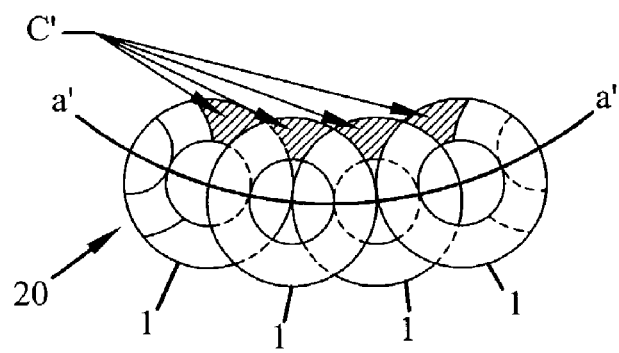
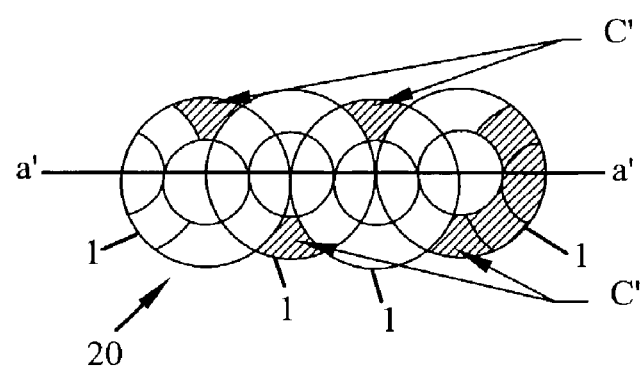
FIG. 10

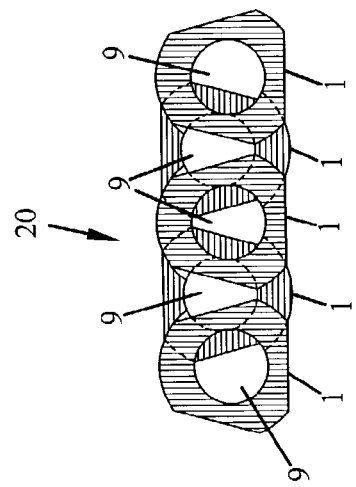
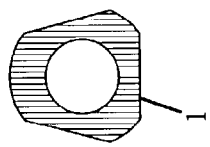
FIG. 17A
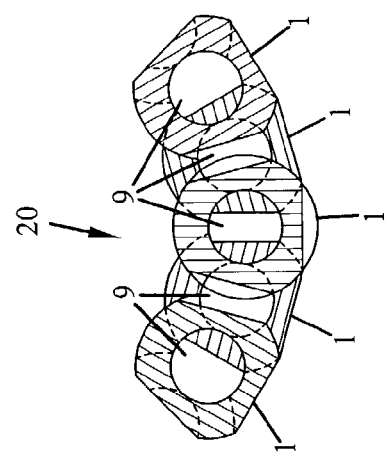

MODULAR SPINAL FUSION DEVICE

This application claims the benefit of priority of U.S. Provisional Patent Application Ser. No. 60/368,950, filed Mar. 29, 2002, entitled "Methods and Apparatus for Low Overhead Enhancement of Web Page and Markup Language Presentations," and which is also claims the benefit of Provisional application No. 60/325,585, filed Sep. 27, 2001, the teachings of which are incorporated herein by reference.

BACKGROUND

1. Field of the Invention

This invention pertains to a surgical implant for fusing one or more bones. More particularly, the invention relates to a modular implant for use in fusing and/or stabilizing adjacent vertebrae.

2. Description of the Prior Art

Chronic low back pain is one of the most common and perplexing problems facing the field of orthopedic surgery. In addition to patient discomfort, chronic low back pain has severe adverse societal impacts including lost income, possible chronic dependence on drugs or alcohol and public relief programs.

In many cases, low back pain can be avoided by preventing relative motion between spinal vertebrae (commonly referred to as intervertebral stabilization). To abate low back pain, intervention is often directed to stabilizing contiguous vertebrae in the lumbar region of the spine.

Surgical techniques are known for use in spinal stabilization. Surgical techniques seek to rigidly join vertebrae that are separated by a degenerated disk. Ideally, the surgery effectively replaces the vertebra-disk-vertebra combination with a single rigid vertebra. Various surgical techniques have developed which attempt to approach or approximate this ideal.

One technique known in the art is to partially remove a degenerated disk and to insert a bone graft into the void formed by the removed disk. Other techniques involve the use of an implant which, acting alone or in combination with bone fragments, is constructed of non-bone materials (e.g., stainless steel, titanium, ceramics, biodegradable polymers, etc.). An example of such implant is shown in U.S. Pat. No. 4,501,269 to Bagby dated Feb. 26, 1985. In Bagby, a large, cylindrical basket is driven into a hole formed between bones that are to be joined. The basket is hollow and is filled with bone fragments that are produced during a boring step. Bone-to-bone fusion is achieved through and about the basket. In Bagby, the hole for the Basket is slightly smaller than the diameter of the basket. This structure results in the spreading of the opposing bone segments upon insertion of the basket. This provides initial stabilization. Eventual fusion of the opposing bone segments results from bone growth through and about the basket.

SUMMARY

The invention provides an implant for use in stabilization of one or more bones, for example, adjacent vertebrae. The implant includes two or more coupled structural elements. Each structural element includes a first end spaced apart from a second end. A side surface extends between the first and second ends and includes at least one recess, wherein two or more structural elements are coupled by matingly engaging one or more recesses.

BRIEF DESCRIPTION OF THE FIGURES

FIG. 1A is a top perspective view of a structural element having a plurality of notches extending from a first end.

FIG. 1B is a top perspective view of a curved modular implant according to one embodiment of the invention.

FIG. 4A is a top perspective view of a structural element having a plurality of notches extending from a first and second end.

FIG. 4B is a top perspective view of a curved modular implant according to another embodiment of the invention.

FIG. 6 is a schematic top view of a modular implant including one or more inserts.

FIG. 7 is a side elevational view of an insert according to the invention.

FIG. 8 is a schematic top view of a modular implant in a clustered configuration.

FIG. 9 is a schematic top view of a modular implant in a curved configuration.

FIG. 10 is a schematic top view of a modular implant in a linear configuration.

FIG. 11 is a schematic side elevational view of a modular implant with structural elements of varying heights to approximate a lordotic angle.

FIG. 12 is a schematic side elevational view of a modular implant including structural elements with non-parallel end surfaces to approximate a lordotic angle.

FIG. 17A is a schematic top view of a structural element having a shape of a triangulated cylinder in cross section.

FIG. 17B is a schematic top view of an alternative modular implant with triangulated cylindrical structural elements in a curved configuration.

FIG. 17C is a schematic top view of an alternative modular implant with triangulated cylindrical structural elements in a linear configuration.

DETAILED DESCRIPTION

Figure 2B:
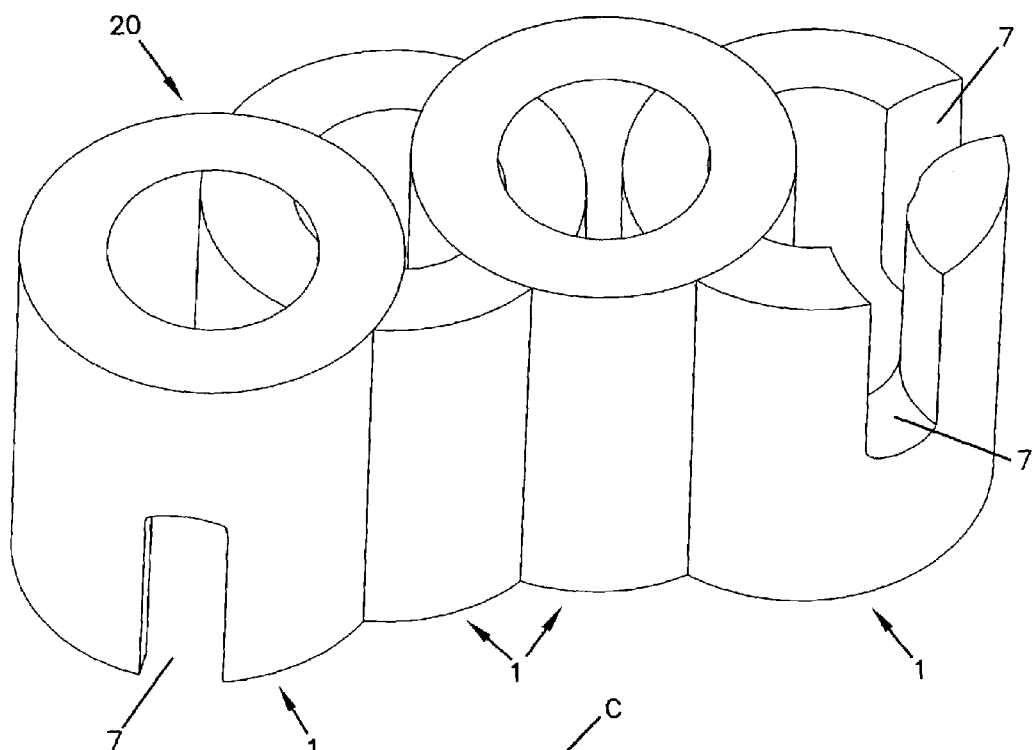
FIG. 2B is a top perspective view of a curved modular implant according to another embodiment of the invention.

I. Overview:

The invention provides a modular implant for fusing one or more bones. In one embodiment, the modular implant can be used to restore intravertebral disc height and stabilize the vertebral column, while allowing intervertebral (interbody) fusion to occur at the implanted spinal level. Although the disclosure focuses on stabilizing and/or fusing adjacent vertebrae, the invention is not so limited. For example, the invention can be used to fuse other bones, including but not limited to, fractures of or separations in a femur, tibia, humerus, or other long bone. Moreover, the implants are suitable for use with or without additional supporting devices, such as rods, screws, hooks, plates and the like.

The modular implant is formed from two or more structural elements that can be assembled, pre-implantation, in a variety of shapes and sizes to accommodate varying patient anatomies and surgical procedures. Alternatively, in some embodiments, the structural element may be assembled during implantation. The structural elements can be assembled to form modular implants having various sizes and shapes (e.g., curved, straight, clustered, lordotic, etc.). If desired, the modular implant can be implanted in a minimally invasive fashion, from either a posterior, anterior, or lateral approach.

The modular nature of the implant allows for the use of structural elements having an aspect ratio greater than 1. In certain uses, an object having an aspect ratio greater than 1 tends to be "unstable" and prone to tipping over. However, according to one aspect of the invention, two or more such structural elements are coupled together, to form an implant with an aspect ratio of less than or equal to 1. In certain embodiments, the allowable dimensions permit structural elements to be constructed from a previously underutilized source of cadaveric bone, for example, the human tibia.

Furthermore, although in certain embodiments a connector or a structural element having one or more protrusions can be used in connection with the modular implant of the invention, in one embodiment, the design advantageously does not require the use of a connector or protrusion to engage the structural elements. Thus, in one aspect of the invention, the design eliminates the need for a connector or protrusion, which may create a locus of weakness, enlarge the overall profile of the modular implant, and/or complicate the assembly of the modular implant.

II. Structural Element

One embodiment of a structural element is shown in FIG. 1A. As shown in FIG. 1A, the structural element 1 includes a first end 2 and a second end 3 spaced apart by an axis A—A of the structural element 1. Generally, a side surface 4 extends between the first end 2 and the second end 3. The side surface 4 of each structural element includes one or more recesses 7 that are configured to matingly engage one or more recesses 7 of another structural element 1 (see FIG. 1B).

In one embodiment, the first 2 and second ends 3 are each load-bearing surfaces that contact the surface of the bone to be fused. For example, when implanted between two adjacent vertebrae in a vertebral column (i.e., one vertebrae is superior to the other), the first end 2 contacts the inferior endplate of a first vertebrae and the second end 3 contacts the superior endplate of the second vertebrae (i.e., the load-bearing surface is the bone-contacting surface). In one embodiment, the first 2 and second 3 end surfaces are substantially parallel (i.e., with one or both end surfaces converging or diverging at an angle of less than about two degrees, more typically less than about one degree), see, for example, FIG. 11. Alternatively, the first 2 and second 3 end surfaces may be non-parallel (i.e., with one or both surfaces converging or diverging), see, for example, FIG. 12. In one embodiment, the first 2 and second 3 end surfaces converge to approximate a lordotic angle $\alpha$. Typically, the end surfaces 2, 3 converge at an angle between about 0 degrees and about 12 degrees, more typically at an angle between about 2 degrees and about 5 degrees, most typically, at an angle between about 2 degrees and about 3 degrees. If desired, the first 2 and/or second 3 end surfaces can be textured to improve frictional engagement with the bone surface of the patient. Examples of textured surfaces include, but are not limited to, grooves, ridges, knurls, teeth, cross-cuts, serrations, and the like.

In one embodiment, the structural element includes a lumen or void. For example, the structural element may include an opening 5 in either the first or second end 2, 3, or both. If desired, the opening 5 in one or more structural elements 1 can extend from the first end 2 to the second end 3 of the structural element 1. Each opening 5 has an inner surface 6.

The section of the structural element 1 disposed between the side surface 4 and the inner surface 6 of the opening 5 can be referred to as a wall 12. That is to say, the wall 12 may be defined by the inner surface 6 of at least one opening 5, at least one load-bearing surface 2, 3, and, the side surface 4 of the structural element 1. The thickness of the wall 12 can be varied, typically the wall 12 has a thickness between about 1 mm and about 5 mm, more typically between about 2 mm and about 4 mm, most typically between about 2 mm and about 3 mm. Generally, for a given outer diameter (OD) a structural element with a thicker wall (i.e., between about 3 mm and about 4 mm) provides a modular implant 20 with a smaller cooperative opening 9 (see discussion below). Likewise, a structural element with a thinner wall (i.e., between about 1 mm and about 2 mm) generally provides a modular implant 20 with a larger cooperative opening 9. Compare, for example, FIGS. 2 and 4.

In one embodiment, one or more recesses 7 extend from the side surface 4 of the structural element 1 to the inner surface 6 of the opening 5 in the structural element 1. The recesses 7 each have an inner surface 13. In one embodiment, the recesses 7 extend from the first 2 or second 3 end, or both, in a direction parallel to the axis A—A of the structural element 1. Recesses 7 that extend from the first 2 or second 3 end (or both) also can be referred to as notches. The portion of the wall 12 of the structural element 1 located between two recesses 7 can be referred to as a column C. The walls of inner surface 13 of the recess 7 are substantially parallel. In an alternative embodiment, the walls of the inner surface 13 of the recess are converging to improve the strength/tightness of fit between the coupled structural elements 1.

Figure 2A:
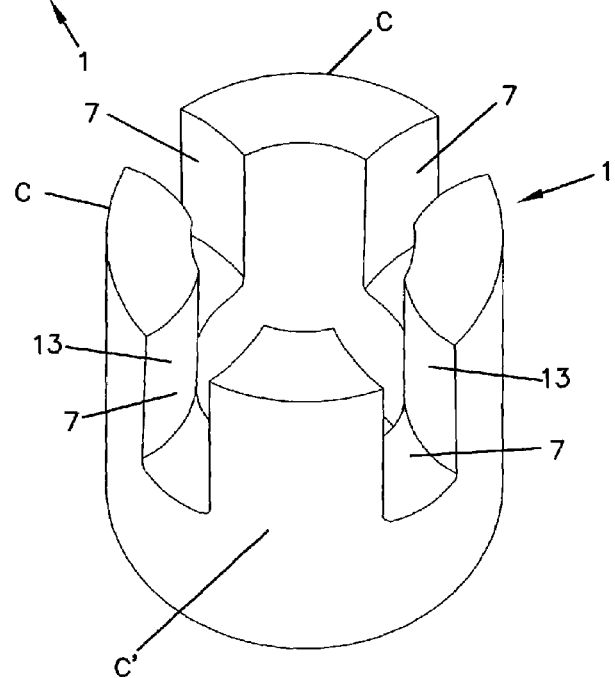
FIG. 2A is a top perspective view of a structural element having a plurality of notches extending from a first end.
Figure 3B:
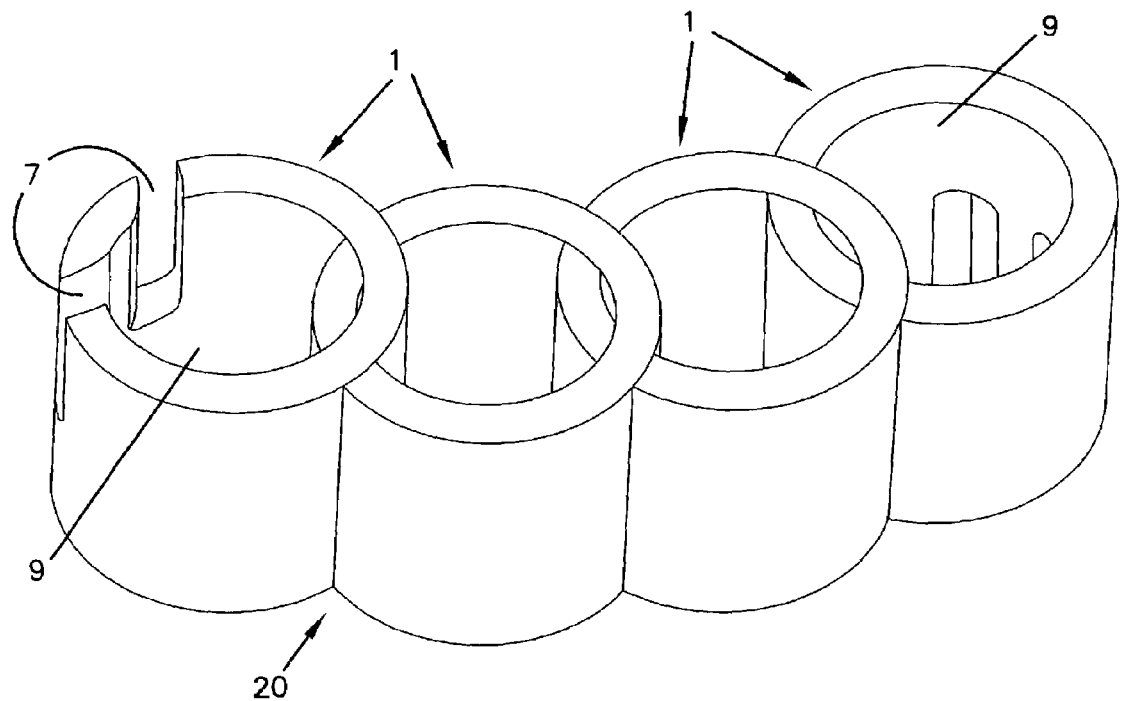
FIG. 3B is a top perspective view of a curved modular implant according to another embodiment of the invention.
Figure 3A:
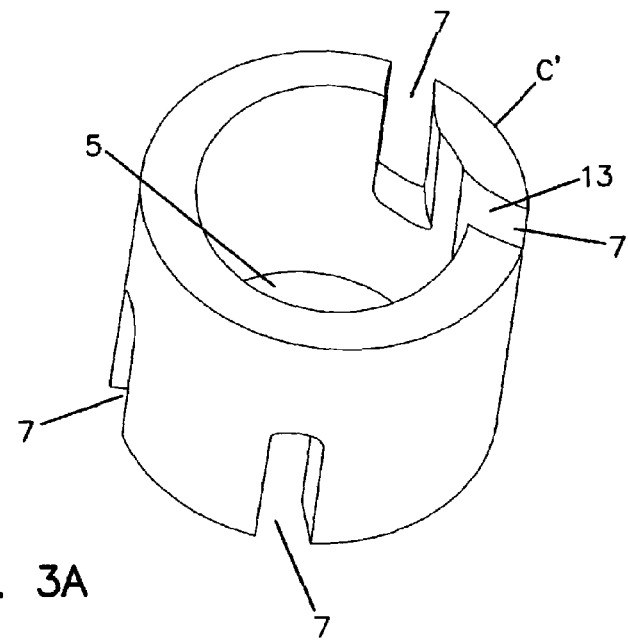
FIG. 3A is a top perspective view of a structural element having a plurality of notches extending from a first and second end.
Figure 5:
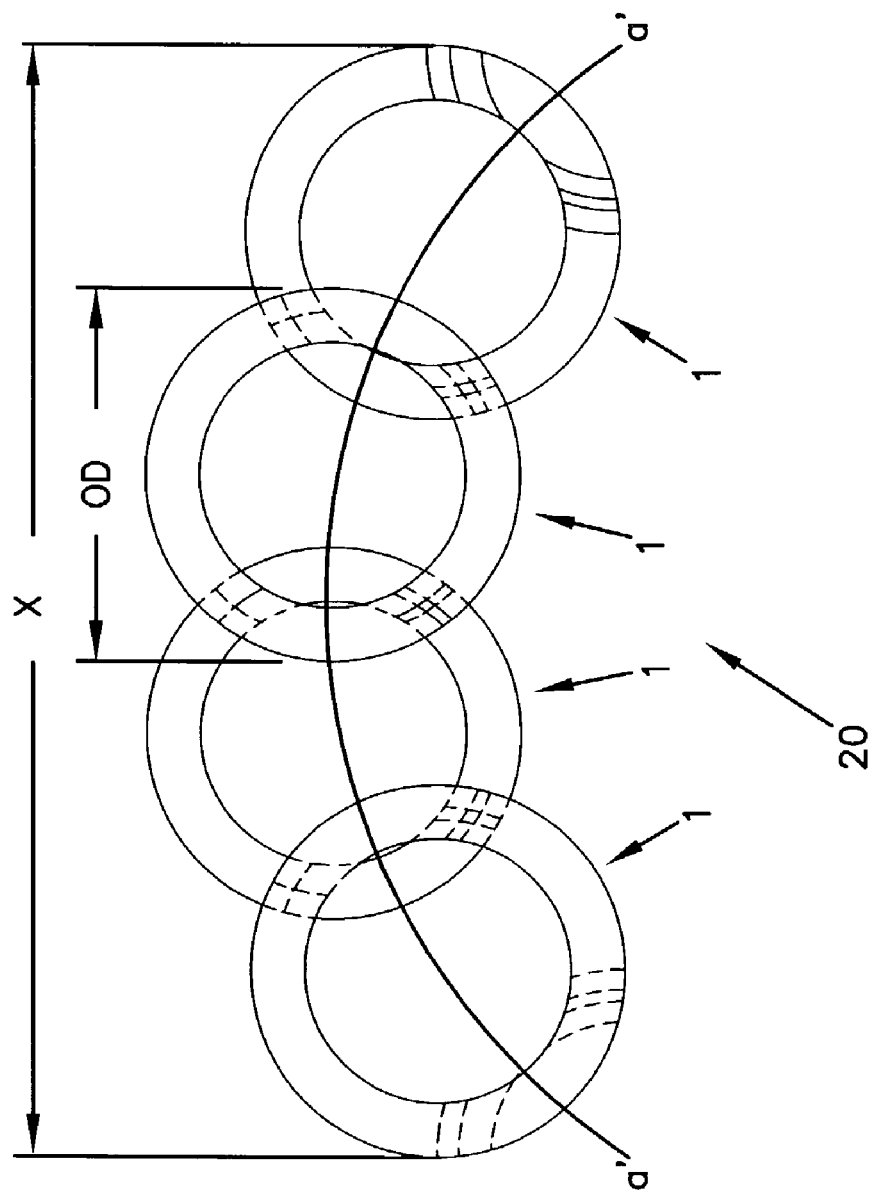
FIG. 5 is a schematic top view of a modular implant according to one embodiment of the invention.
Figure 13:
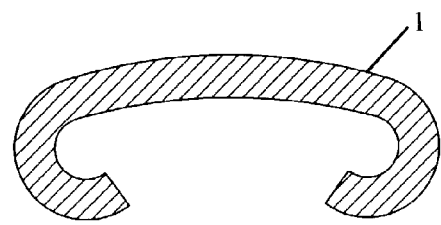
FIG. 13 is a schematic top view of an alternative structural element.
Figure 14:
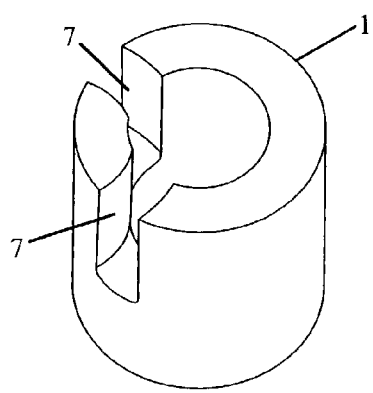
FIG. 14 is a side elevational view of an alternative structural element.
Figure 15:
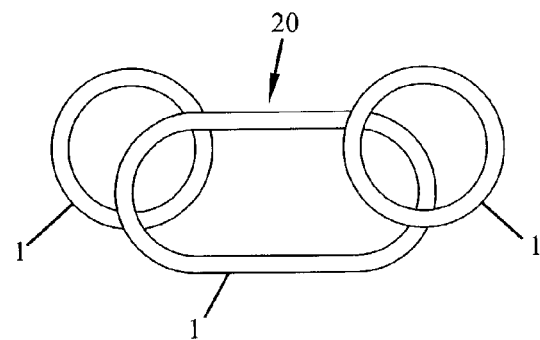
FIG. 15 is a schematic top view of an alternative modular implant with structural elements having differing shapes in cross section.
Figure 16:
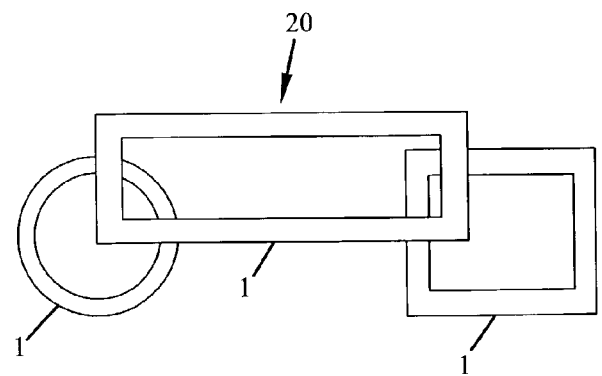
FIG. 16 is a schematic top view of an alternative modular implant with structural elements having differing shapes in cross section.

In some cases, it may be desirable to form a structural element 1 having a plurality of evenly spaced recesses 7. In one embodiment, the plurality of recesses 7 are evenly spaced around the perimeter (p). In another embodiment, the recesses 7 are not evenly spaced around the perimeter (p). In one embodiment, the recesses 7 are configured as notches that are not evenly spaced around the perimeter (p) of the structural element 1. In this embodiment, the structural element 1 includes recesses 7 that define at least one minor column C'. As used herein, the term "minor column" C' refers to a column whose radial arc is smaller than that of at least one other column C of the structural element 1. For example, in the embodiment shown in FIG. 1A, the structural element 1 includes four recesses 7 that extend from a first end 2 to define four columns C. The recesses 7 are spaced such that they define at least one minor column C'. In one embodiment, the minor column C' is smaller than the other columns C. The notches 7 can all extend from one side surface, as shown in FIGS. 1A and 2A, or the notches 7 can extend from both side surfaces, as shown in FIGS. 3A and 4A. In one embodiment, the modular implant 20 may include one or more "end" structural elements 1 that include recesses 7 that do not mate with recesses 7 of another structural element 1 (see, for example, FIGS. 2B, 3B and 4B). In an alternative embodiment, specialized "end" structural elements 1 can be provided, such that the resulting modular implant 20 does not include an "end" structural element with "unmated" recesses 7 (see, for example, FIG. 1B)

In some cases, it may be desirable to provide one or more recesses 7 with a textured inner surface 13 to enhance frictional engagement between the recesses 7 when the structural elements 1 are coupled. Examples of suitable textured surfaces include grooves, knurls, etc. Specifically oriented patterns can be designed to enhance "locking" between structural elements 1.

The structural element 1 can have any suitable shape (see, for example, FIGS. 1–18). In one embodiment, at least one structural element has a substantially round shape in cross-section, for example, the structural element 1 may be circular, oval, or elliptical in cross-section. The term "rounded" refers to a structural element 1 with at least one arcuate surface. Therefore, the term "rounded" also includes structural elements 1 that have the shape of a "truncated circle" (or "truncated cylinder") in cross section. As used herein, the term "truncated circle" refers to a shape formed by cutting one or more flat surfaces into the circumference of a circle. For example, a "truncated circle" can be a shape formed by cutting a circle in half, to form a semi-circle. In another example, a "truncated circle" is a "triangulated circle." As used herein, the term "triangulated circle" refers to a shape that is created by cutting three flat surfaces of a circle. Generally, a "triangulated circle" has a shape of a triangle, but the angles (or corners) are rounded. In another embodiment, the structural element has a shape in cross-section that is angled, for example, the structural element 1 may be square, triangular, rectangular, trapezoidal, or a rhombus in cross section. As used herein, the term "angled" refers to a shape formed by the intersection of two planes. Included within the scope of this invention are structural elements having a shape that is both "rounded" and "angled" in cross section. In one embodiment, the structural element 1 is substantially in the shape of a cylinder (see, for example, FIGS. 1–4). In another embodiment, the structural element 1 is in the shape of a triangulated cylinder (see, for example, FIGS. 17A–C).

The structural element 1 can be any size suitable for the site of implantation. For example, for use in spinal fusion, a structural element 1 can have a major width ranging between about 7 mm to about 28 mm and a height between about 5 mm to about 20 mm. The size of the structural element 1 also may vary depending on the desired surgical procedure and patient anatomy. Generally, a structural element 1 for use in constructing a modular implant 20 for fusing cervical vertebrae of an adult human patient will have a major width between about 5 mm to about 10 mm and a height between about 5 mm to about 9 mm. In contrast, a structural element 1 for use in constructing a modular implant 20 for fusing lumbar vertebrae of an adult human patient will generally have a major width between about 7 mm to about 28 mm and a height between about 8 mm to about 20 mm.

The "major width" of a structural element 1 can be determined by calculating the length of a vector (V) extending in a direction perpendicular from a first point on the perimeter (p) of the side surface of the structural element to a second point on the perimeter (p) of the side surface. The length of the vector (V) having the longest length is the "major width" of the structural element 1. Generally, for a cylindrical structural element 1, the "major width" corresponds to the outer diameter (OD) of the cylinder. For a structural element having an irregular shape in cross section (e.g., an oval, rectangular, triangulated cylinder, trapezoid, or other irregular shape), the "major width" can be determined as described above.

The "height" of a structural element 1 can be determined by measuring the distance between the first 2 and second 3 end surfaces. If the first 2 and second 3 end surfaces are not parallel, the greatest distance therebetween is used to assess the "height" of the structural element 1.

The structural element 1 can be constructed from any suitable biocompatible material, such as bone, metal, ceramic, plastic, and combinations thereof. Suitable bone materials include materials from human (including both allograft and autograft) and animal sources (e.g., xenograft, for example, bovine sources), typically from long bones such as the tibia, femur, and humerus. Suitable plastics include polyetheretherketone (PEEK). The plastic can be used with or without carbon fiber (i.e., to enhance structural strength). Suitable metals include titanium and titanium alloys (such as Ti 6AI 4V), memory metals such as Nitinol™, stainless steels (such as 306L) and porous metals. If desired, the structural element can be constructed from an osteoinductive material, osteoconductive material, radio opaque material, radiolucent material, and combinations thereof.

In one embodiment, the structural element 1 is constructed from a bone material, for example, from a tibial source (such as a human tibial source, typically, a human cadaveric source). Although the tibia is the second largest bone of the human skeleton, it is generally not used in fusion implants due to the limited dimensions of cortical bone that can be harvested. However, because the structural elements 1 of the invention are coupled prior to implantation, an expanded range of sources of cortical bone, such as the tibia, now can be used.

Figure 18:
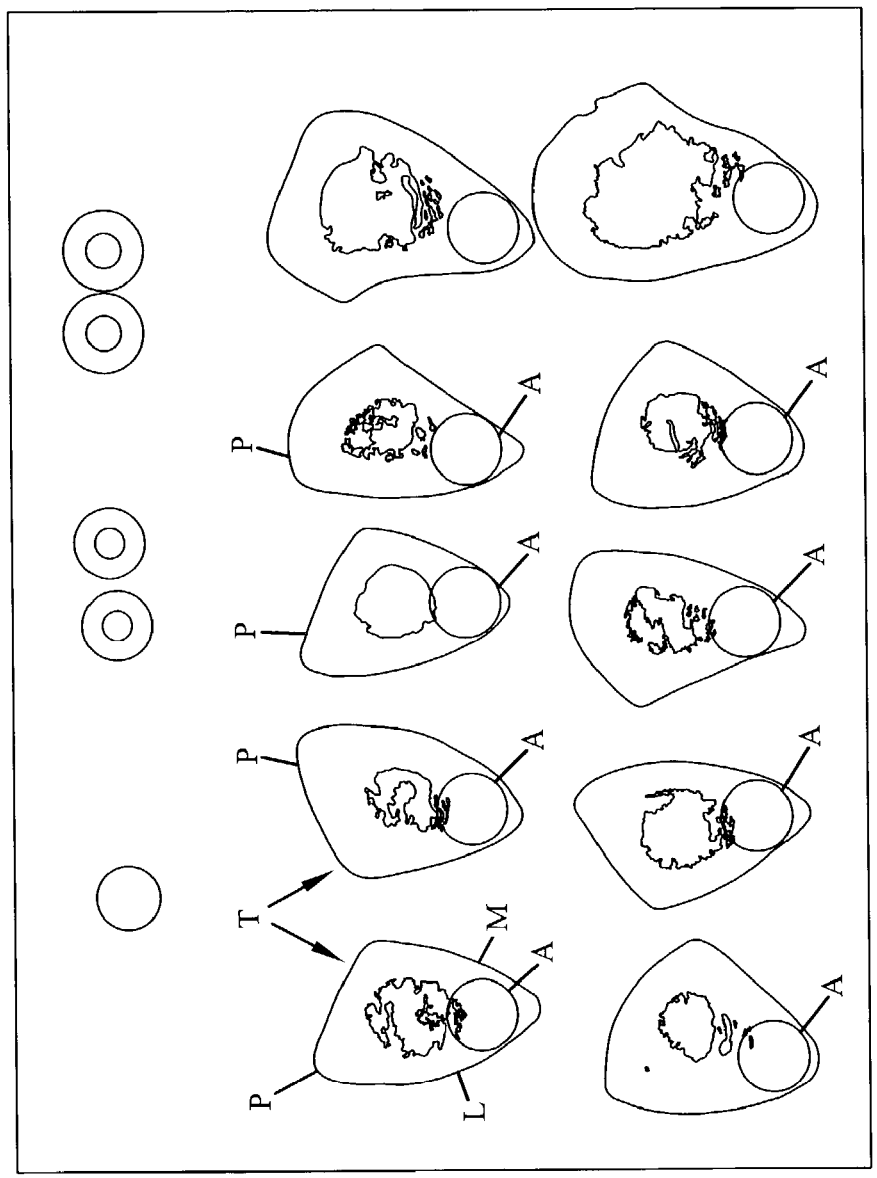
FIG. 18 is a photograph showing the location from which cylinders for constructing structural elements may be obtained from human cadaveric tibia.
Figure 19:
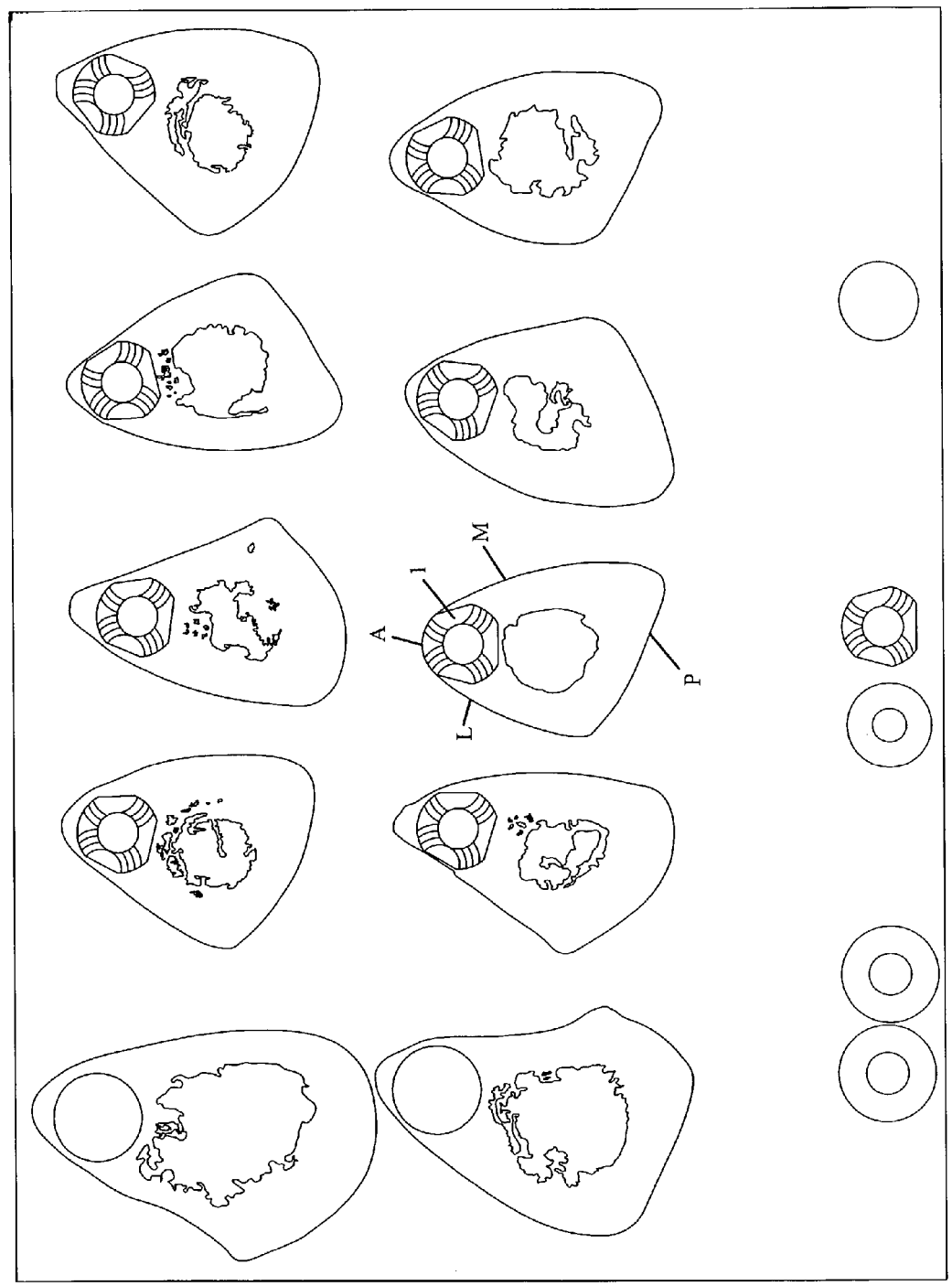
FIG. 19 is a photograph with a schematic overlay showing the location from which cylinders for constructing structural elements may be obtained from human cadaveric tibia.

FIG. 18 shows a possible location from which cortical bone can be harvested from a human tibia (T). As shown in FIG. 18, the shaft of the tibia is approximately triangular in transverse section with medial (M), lateral (L) and posterior (P) surfaces formed from cortical bone. When viewed in cross section, the three surfaces intersect to define a medullary cavity. The medial (M) and lateral (L) surfaces intersect at an anterior (A) junction, which generally has a greater dimension than the medial (M), lateral (L) and posterior (P) surfaces. Thus, it may be desirable to harvest cortical bone from the tibia at the anterior (A) junction. In one technique, cylinders of cortical bone are machined from the anterior (A) junction of the tibia. If desired, "triangulated" cylinders can be machined from the anterior (A) junction, as shown in FIG. 19. It may be desirable to machine "triangulated" cylinders as certain segments of a long bone (e.g., a tibia) have an anterior junction of insufficient dimensions to provide a completely round structural element. Triangulated cylinders offer the advantage of a larger cooperative opening and alternative final implant geometries when coupled together.

Generally, when the structural element 1 is constructed from bone material obtained from a tibial source, the structural element has a major width of less than about 11 mm. Typically, a structural element 1 harvested from a human tibia will have a major width between about 8 mm and about 11 mm, more typically between about 8 mm and about 10 mm, most typically between about 8 mm and about 9 mm, particularly if the bone is harvested from the anterior junction of the tibia.

II. Modular Implant

The invention also provides a modular implant 20 constructed by coupling two or more of the structural elements 1, described above. Advantageously, in one embodiment, the structural elements 1 can be coupled, prior to implantation, to form a "customized" modular implant 20 designed for the anatomy of a particular patient and/or a particular surgical procedure.

Modular implants 20 having a variety of shapes and sizes can be constructed, depending on the number, orientation and assembly of the structural elements 1. Typically, the modular implant includes between 2 and 10 structural elements 1 that are coupled together. Modular implants 20 having varying heights also can be created, using structural elements 1 having different heights. For example, a modular implant 20 suitable for use in fusing lumbar vertebrae may be assembled using structural elements 1 having a height between about 8 mm and about 20 mm. Alternatively, a modular implant 20 suitable for use in fusing cervical vertebrae may be assembled using structural elements 1 having a height between about 5 mm and about 9 mm. A "stepped" modular implant 20 also can be created for maintaining a lordotic angle by assembling two or more structural elements 1 of varying heights (see, for example, FIG. 11). If desired, a "lordotic" modular implant 20 can be assembled using structural elements 1 having first 2 and second 3 end surfaces that are angled with respect to each other (see, for example, FIG. 12). In one embodiment, a modular implant 20 includes at least one structural element 1 that has a height that is different than the height of at least one other structural element 1. In another embodiment, a plurality of structural elements 1 having various heights are coupled to form a modular implant. Additionally, one or more structural elements 1 constructed from different materials (e.g., PEEK, bone, metals, or ceramic) can be combined in a single modular implant 20. For example, metal and bone structural elements 1 can be coupled to create a modular implant 20 having the enhanced strength characteristics of metal and the biological advantages of bone (e.g., creeping substitution, osteoconductivity, etc.). In one embodiment, at least one structural element 1 is constructed from a material that is different than at least one other structural element 1. One or more structural elements 1 having differing shapes in cross-section also can be coupled together to form a modular implant 20 (see, for example, FIGS. 15 and 16). In one embodiment, at least one structural element has a shape in cross-section that is different from at least one other structural element.

Generally, one or more recesses 7 extend from the side surface 4 of the structural element to the inner surface 6 of the opening 5 in the structural element. Typically, the recess 7 has a width that corresponds to a width of the wall 12 of the structural element 1 it is configured to matingly engage. Alternatively, the recess 7 width may be somewhat smaller than the wall 12 width (e.g., to provide a "press-fit" coupling of the structural elements). In a further alternative embodiment, the recess 7 width may be somewhat larger than the wall 12 width (e.g., to provide a degree of "play" and/or to accommodate the inclusion of a bonding agent or in the coupling of the structural elements).

As described above, the first 2, second 3, or both, end surfaces (e.g., the bone-contacting surface) can be smooth or may include a textured pattern to enhance frictional engagement with the bone surface. The textured pattern of the structural elements may align or be unidirectional when the structural elements 1 are coupled, or the textured pattern of the various structural elements 1 may run in different directions. In an alternative embodiment, the side surfaces of the structural elements may function as the bone-contacting surface, and thus may include similar textured patterns.

The structural elements 1 of the invention can be assembled to form modular implants 20 having various shapes. For example, the structural elements 1 can be assembled to form clustered, curved, and/or linear implants (see, FIGS. 8, 9, and 10, respectively). As used herein, the term "linear" refers to a modular implant 20 in which each structural element 1 is adjacent to no more than two other structural elements, and wherein a line connecting the axes A—A of the structural elements 1 (see e.g., line a'—a' of the modular implant in FIG. 10) is generally linear. Similarly, the term "curved" refers to a modular implant 20 in which each structural element 1 is adjacent to no more than two other structural elements, wherein a line connecting the axes A—A of the structural elements 1 (see e.g., line a'—a' of the modular implant of FIG. 9) is curved. The curvature can be unidirectional, like the letter "C"; bi-directional, like the letter "S"; or even multi-directional (e.g., sinusoidal). The modular implants may also be assembled both into shapes including linear and curves sections (e.g., a "U" shaped modular implant). The radius of curvature can be altered by changing the location and/or orientation of the recesses 7 around the perimeter (p) of the structural element 1. Generally, a curved modular implant 20 will tend to have more stability in a direction transverse to the axis a'—a' than a linear modular implant 20. Suitable radii of curvature include those between about 18 and about 50.

In one embodiment, the same set of structural elements 1 can be used to create a linear or a curved modular implant depending upon the orientation of the recesses 7 of the structural element 1. For example, each structural element may have a perimeter (p) and a plurality of recesses 7 that are not evenly spaced around the perimeter (p), such that the recesses 7 define at least one minor column C', which is smaller than the other columns. To assemble a curved implant 20, the minor column C' is aligned towards the inside of the curve. In contrast, to assemble a linear implant 20, the minor column C' is placed on alternating sides of the implant. (See, FIGS. 9 and 10, respectively).

If desired, the length of a modular implant 20 resulting from assembly of a specified number of structural elements 1 can be varied by altering the spacing between the recesses. For example, a curved implant constructed from five structural elements 1, each having an outer diameter (OD) of 8 mm can have a length (X) of 22 mm. However, if a curved implant is constructed from five structural elements 1, each having an outer diameter (OD) of 8 mm spacing, but the spacing between the recesses 7 is increased, the curved implant can have a length (X) of 28 mm. (See, FIG. 5).

Generally, the modular implants 20 of the invention tend to be stable, even when the structural elements 1 may be unstable (e.g., prone to tipping). That is because, in certain embodiments, the modular implant 20 has an aspect ratio less than or equal to one. In alternative embodiments, the modular implant includes or a radius of curvature that improves stability, even when individual structural elements 1 having an aspect ratio of greater than one are used. Thus, the structural elements 1 of the invention can be constructed using sources that may not otherwise be suitable, for example, tibial bone material (see discussion above) and/or be used in a wider array of indications (e.g., cervical and lumbar fusion procedures) than previously known.

As used herein, the term "aspect ratio" of a structural element refers to the ratio of the height of a structural element to the width of at least one load-bearing surface of the structural element. The width of a structural element having a circular cross section can be determined by calculating the diameter of the circle. For a structural element having an irregular shape in cross section (e.g., oval; rectangular, including square; triangle; trapezoid; or other irregular shape), the width the of the load-bearing surface can be calculated by calculating the length of a vector extending in a direction perpendicular from a first point on the perimeter of the load-bearing surface to a second point on the perimeter of the load-bearing surface. The vector having the shortest length is used as the width (the "minor width") of the load-bearing surface when calculating the aspect ratio. For structural elements having load-bearing surfaces that are not parallel (e.g., a structural element approximating a lordotic angle), the greatest height of the element is used to calculate the aspect ratio. In one embodiment of the invention, the modular implant 20 includes at least one structural element 1 that has an aspect ratio that is different than the aspect ratio of at least one other structural element 1. In another embodiment, at least one structural element 1 has an aspect ratio of greater than one, wherein the modular implant 20 has an aspect ratio that is less than or equal to one.

In one embodiment, when the structural elements 1 are coupled together to form a modular implant 20, the structural elements are in an "overlapping" configuration. As used herein, the term "overlapping" means that a width of the modular implant is less than the sum of the width of the structural elements 1. Generally, this means that the axes of the structural elements are offset, while the walls of the structural elements 1 interlock. In one embodiment, both the first 2 and second 3 end surfaces of each structural element 1 remain bone-contacting surfaces, even when the structural elements are interlocked. Typically, in this embodiment, the axes of the structural elements 1 are parallel. In one embodiment, when in the "overlapping" configuration, the inner surface 6 of at least one structural element 1 faces the inner surface 6 of at least one another structural element 1.

Although not necessary, a biocompatible bonding agent can be used to secure the coupling of the structural elements 1, if desired. Examples of suitable biocompatible bonding agents include polymethylmethacrylate (PMMA), and fibrin glue. Alternatively, or additionally, the modular implant 20 can be hydrated (for example, by immersing the implant 20 in a saline solution at a temperature between about 18° C. and about 25° C., for between about 30 minutes and about 45 minutes) to cause the coupled structural elements 20 to swell and increase the mechanical locking force between them. Hydration is particularly suitable when the modular implant 20 is assembled from structural elements 1 constructed from a hydratable material, for example, a bone material.

In one embodiment, the modular implant 20 includes a biologically active agent, such as a bone growth enhancing material or an antibiotic. As used herein, the term "biologically active agent" refers to, without limitation, physiologically or pharmacologically active substances that act locally or systemically in the body. Of particular suitability for this invention are biologically active agents that are osteoinductive or osteoconductive. Examples of materials that enhance bone growth and/or fusion include, but are not limited to, bone or bone substitute products such as human growth factors, bone morphogeneic proteins (BMP), cancellous bone, autograft bone, allograft bone, etc. Examples of antibiotics include antimicrobials and antibacterials.

As described above, one or more structural elements 1 may include a lumen or void. For example, the structural element may include at least one opening 5 in at least end surface 2, 3, wherein each opening 5 has an inner surface 6. If desired, the biologically active agent can be placed within the void or opening 5.

In another embodiment, the implant 20 includes one or more cooperative openings 9 defined by the inner surface 6 of an opening 5 in a first structural element 1 and a side surface 4 of an overlapping structural element 1. If desired, one or more inserts 11 can be configured to be received within a cooperative opening 9 of the implant 20 (see, for example, FIGS. 6 and 7). The insert 11 can be constructed from any suitable material. In one embodiment, the insert 11 includes a biologically active agent. As shown in FIGS. 17B–C, structural elements 1 formed as a "triangulated cylinder" tend to increase the size of the cooperative opening 9 in the modular implant 20.

III. Method

The invention also includes a method for fusing one or more bones. Generally, the method includes obtaining or providing two or more structural elements 1, described above. The recesses of the structural elements 1 are engaged to form a modular implant 20, which is then inserted between the bones to provide stability and/or enhance fusion. Alternatively, the structural elements may be engaged during and/or at the site of implantation.

In one embodiment, the implant 20 of the invention is used to facilitate fusion of adjacent vertebrae, including cervical, thoracic, and lumbar vertebrae. The assembled implant 20 can be inserted into the disc space via an anterior approach, posterior, or lateral approach. Those of skill in the art are familiar with methods for implanting spinal fusion devices from these approaches, including open, and minimally invasive, for example, laproscopic procedures. In some embodiments, it may be desirable to assemble the structural elements 1 to form a clustered implant 20 when used in connection with an anterior approach. In other embodiments, when used in connection with a posterior approach, it may be desirable to assemble the structural elements 1 to form a curved or linear implant 20.

According to the invention, the medical practitioner can assemble the structural elements 1 to form a modular implant 20 suitable for the particular anatomy of the patient or surgical procedure used.

IV. Inserter Tool

Figure 20:
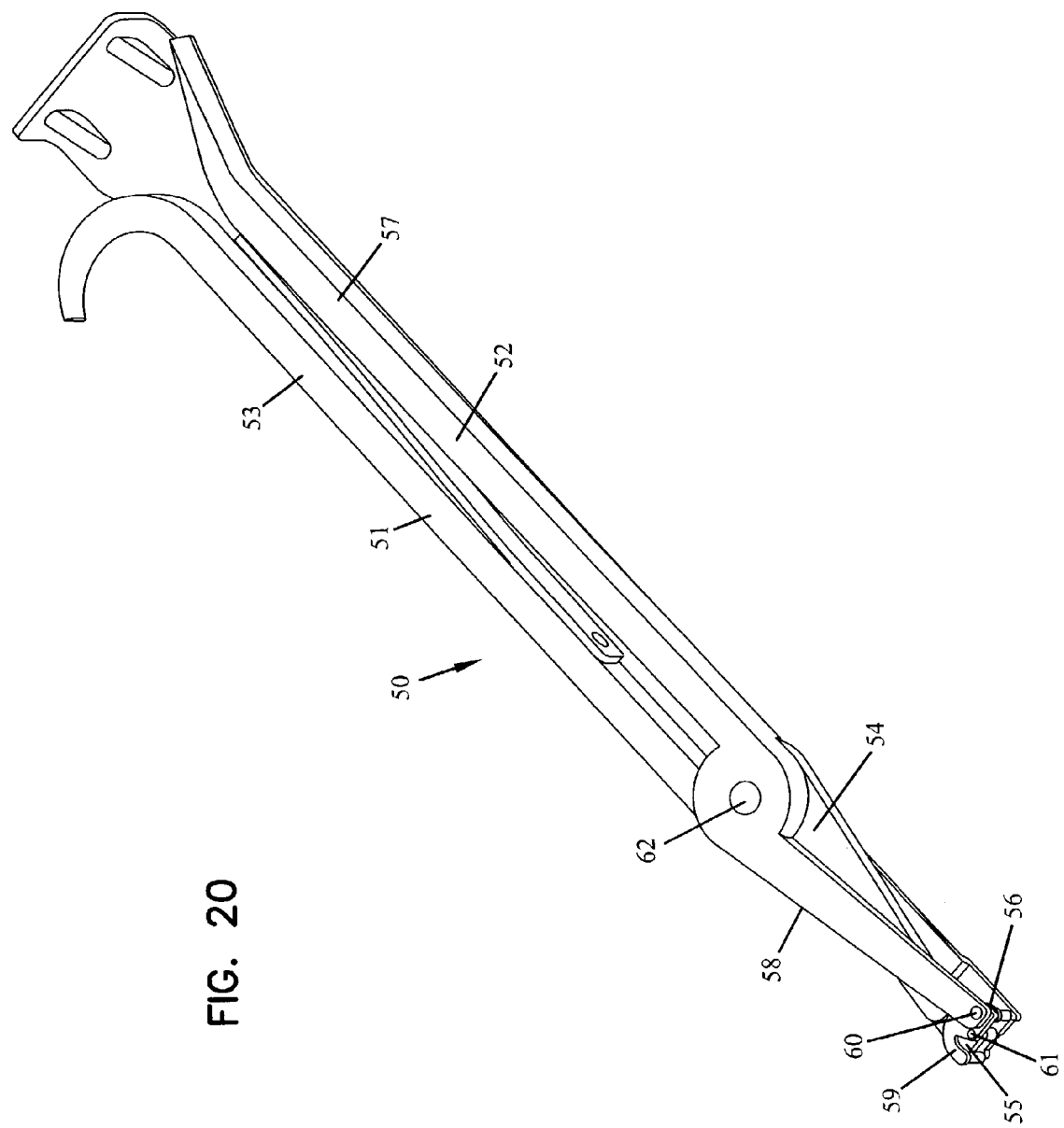
FIG. 20 is a top perspective view of an inserter tool.

The invention also includes an inserter tool 50 useful for handling and/or implanting the modular implant 20, described above. The inserter tool 50 includes a pair of intersecting arms and a common axis interconnecting the intersecting arms wherein the arms are capable of rotating around the common axis (FIG. 20).

The inserter tool 50 includes first 51 and second 52 arms. The first arm 51 includes a first proximal shaft 53 and a first distal shaft 54. A first moveable head 55 is rotatably connected to the first distal shaft 54 at a first axis 56. The second arm 52 includes a second proximal shaft 57 and a second distal shaft 58. A second moveable head 59 is rotatably connected to the second distal shaft 58 at a second axis 60 and connected to the first movable head 55 at a third axis 61. Thus, the first 51 and second 52 arms are pivotally connected at a fourth axis 62 and are capable of rotating around the fourth axis 62.

If desired, the inserter tool can include a biasing member configured to hold the first proximal shaft 53 and second proximal shaft 57 in a spaced apart relationship. The inserter tool 50 also may include a base member 63 attached to the first 51 and second 52 arms at the third 61 and fourth 62 axes.

Figure 21:
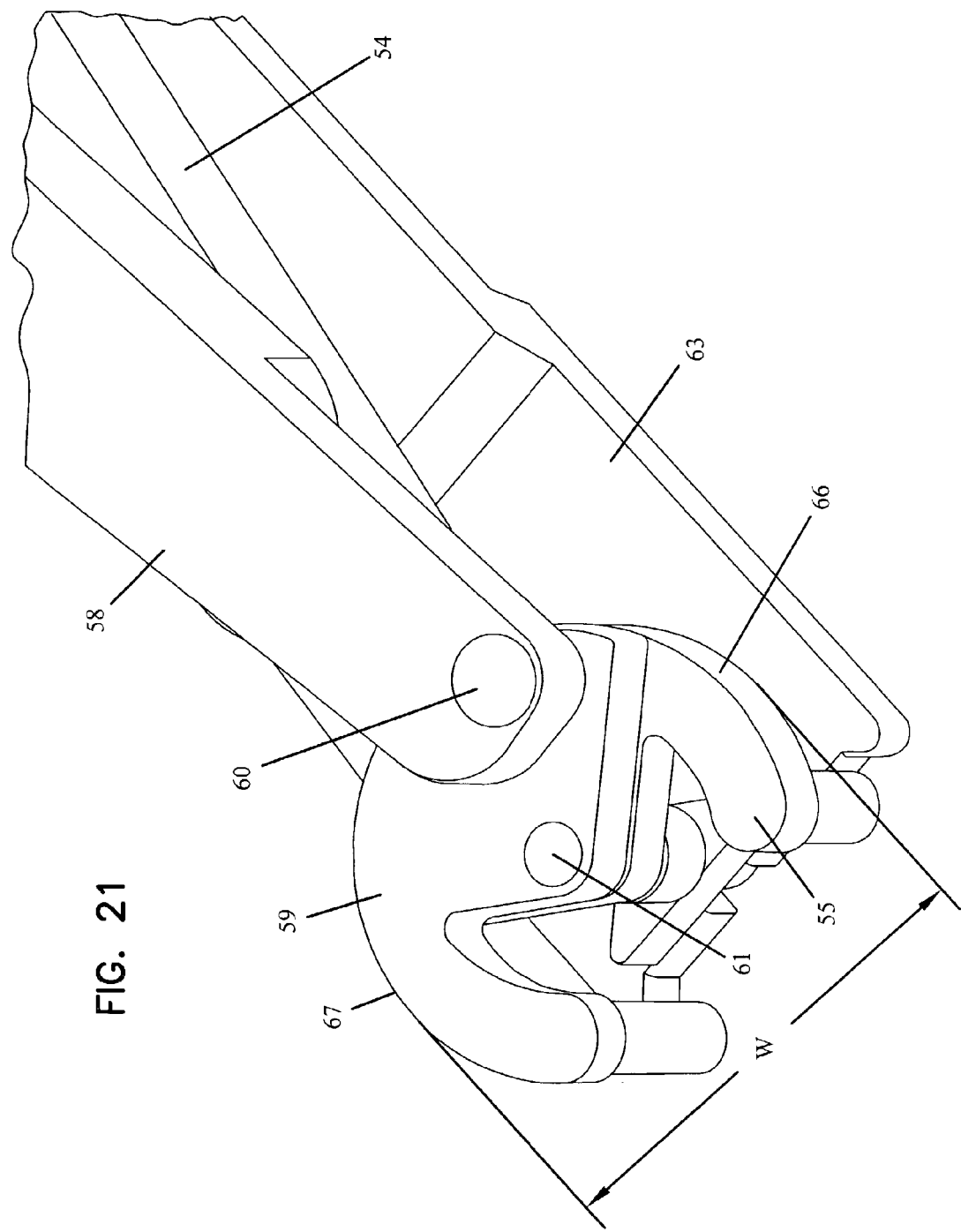
FIG. 21 is a close-up of the jaws of the inserter tool of FIG. 21.

Generally, the first 55 and second 59 moveable heads span a width (W) when engaging the modular implant 20. As used herein, the "width" spanned by the first moveable head 55 and second moveable head 59 refers to the distance between the first exterior surface 66 of the first moveable head 55 and the second exterior surface 67 of the second moveable head 59. Preferably, the width (W) spanned by the first 55 and second 59 moveable heads when engaging the modular implant 20 is no greater than a major width of at least one structural element 1 of the implant 20. (FIG. 21) The clamp can be constructed using any suitable material, including metal, such as stainless steel or titanium or plastics such as injection-molded plastic.

Figure 22:
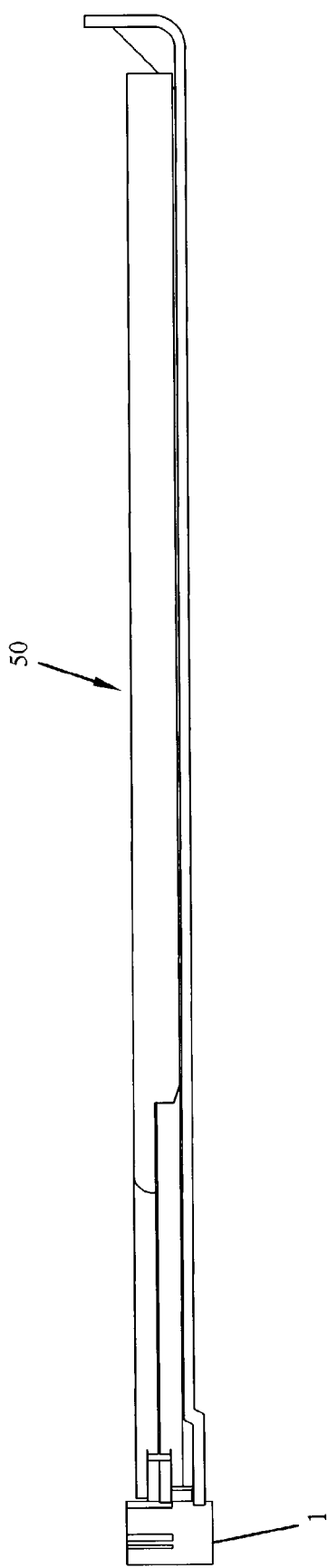
FIG. 22 is a side elevational view of an inserter tool engaging a structural element.
Figure 23:
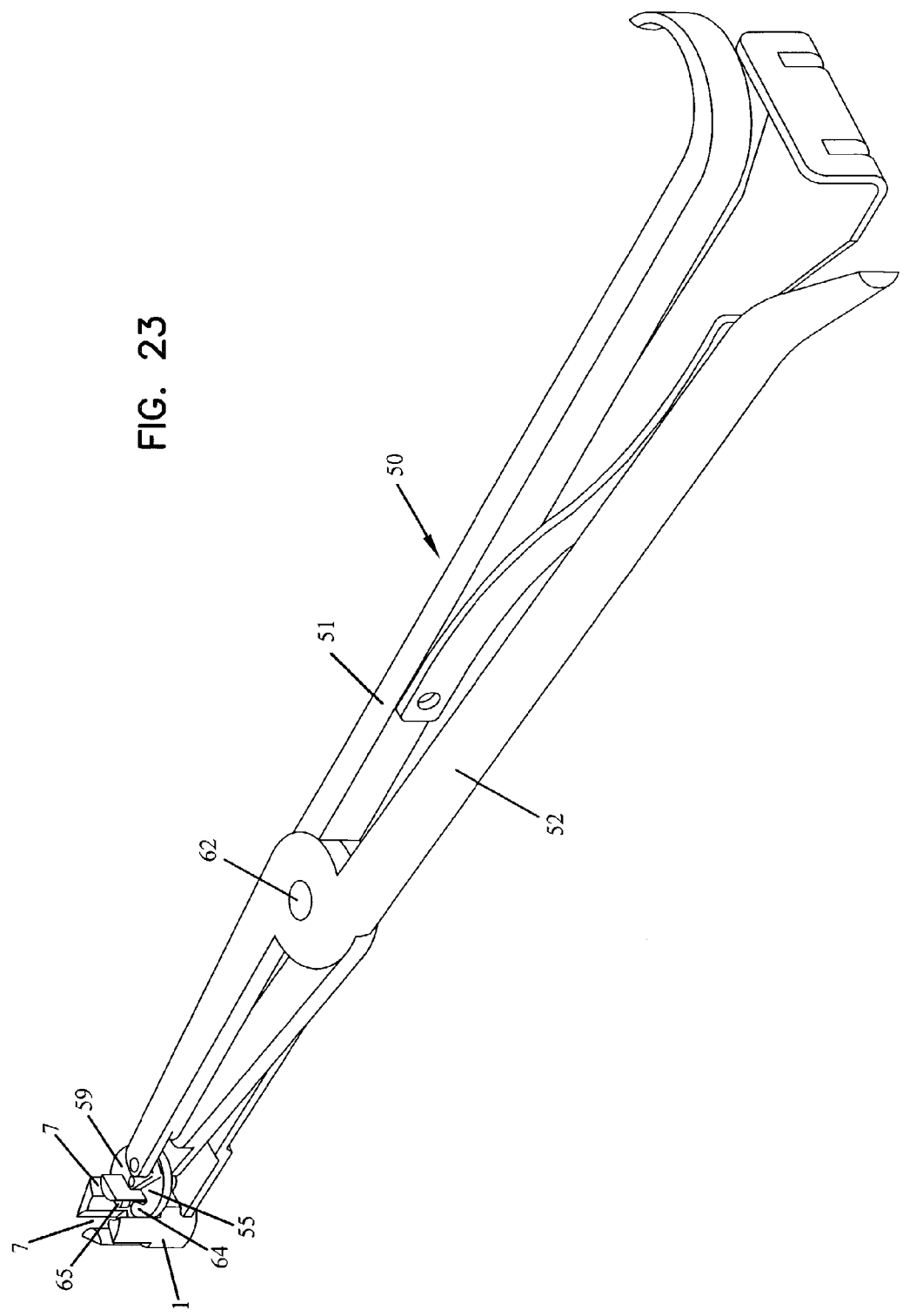
FIG. 23 is a perspective view of the inserter tool of FIG. 23, shown from the rear.
Figure 24:
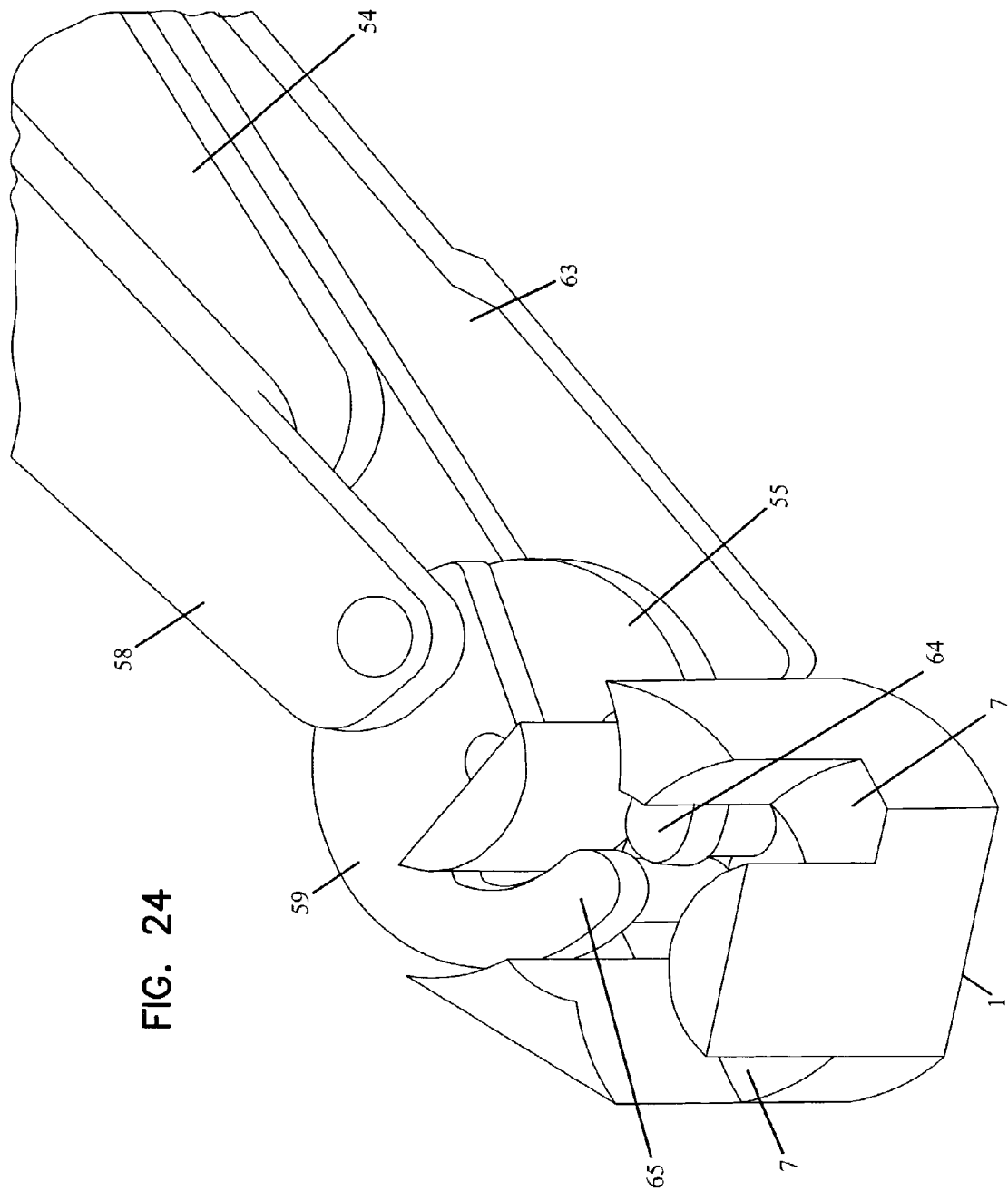
FIG. 24 is a close-up of the jaws of an inserter tool engaging a structural element.

In use, the arms 51, 52 of the inserter tool 50 are rotated apart and a modular implant 20 is positioned between the first 55 and second 59 moveable head. The arms 51, 52 of the inserter tool 50 are then rotated towards one another to engage the modular implant 20. In one embodiment, the first moveable head 55 includes a first projection 64 configured to engage a first recess 7 of the modular implant 20. Likewise, the second moveable head 59 includes a second projection 65 configured to engage a second recess 7 of the modular implant 20 (FIGS. 22–24). Alternatively, the first 55 and second 59 moveable heads are configured to frictionally engage the side surface 4 of at least one structural element 1 of the modular implant 20.

Having disclosed the invention, modifications and equivalents of the disclosed concepts may occur to one skilled in the art. It is intended that the scope of the present invention not be limited to the specific embodiment disclosed, but shall include such modifications and equivalents.

What is claimed is:

1. A modular implant for implantation between first and second adjacent vertebral bodies, the implant comprising:
    a first and a second structural element, each said element including
    a first end spaced apart from a second end by a side surface, and
    one or more recesses in the side surface, wherein the recesses comprise notches extending within the side surface from the first end,
    wherein in each structural element the first end is spaced apart from the second end by an inner side surface and an outer side surface, the recesses extending only partially from one end of each structural element and extending fully from the outer side surface to the inner side surface, of each structural element
    wherein the first and second structural elements are coupled by engaging one or more recesses and wherein, when implanted, the first end of each of the first and second structural elements engages one of the first and second vertebral bodies and the second end of each of the first and second structural elements engages the other of the first and second vertebral bodies.

2. The implant according to claim 1, wherein at least one structural element comprises a wall defined by an inner surface of at least one opening, at least one load-bearing surface, and a side surface of the structural element.

3. The implant according to claim 2, wherein each structural element has a perimeter, wherein at least one structural element has a plurality of recesses defined in at least one load-bearing surface.

4. The implant according to claim 2, wherein coupling of the two structural elements essentially doubles the load bearing surface of the implant.

5. The implant according to claim 1, wherein at least one structural element has a shape in cross-section that is rounded.

6. The implant according to claim 5, wherein the rounded shape in cross-section is selected from a circle, an oval, an ellipse, and a triangulated circle.

7. The implant according to claim 1, wherein at least one structural element has a shape in cross-section that is different from at least one other structural element.

8. The implant according to claim 1, wherein at least one structural element is constructed from a material selected from bone, metal, ceramic, plastic, and combinations thereof.

9. The implant according to claim 1, comprising a plurality of structural elements having varied heights, such that the structural elements, when in an overlapping configuration, approximate a lordotic angle between at least two adjacent vertebrae.

10. The implant according to claim 1, further comprising first and second load bearing surfaces parallel to one another.

11. The implant according to claim 1, further comprising a bone growth enhancing material.

12. The implant according to claim 1, wherein an inner surface of at least one structural element faces an inner surface of at least one other structural element when the structural elements are in an overlapping configuration.

13. The implant according to claim 1, wherein at least one structural element is substantially cylindrical in shape, and at least one of the structural elements includes a void.

14. The implant according to claim 1, wherein the first and second structural elements each includes a sidewall extending between the first and second ends, wherein the sidewalls of the first and second structural elements overlap when the first and second structural elements are coupled.

15. The implant according to claim 1, wherein at least one structural element has an aspect ratio of greater than 1, and the modular implant has an aspect ratio less than or equal to 1.

16. The implant according to claim 1, wherein at least one structural element has a height between about 5 mm and about 20 mm and a width between about 7 and about 28 mm.

17. The implant according to claim 1, wherein the recess in the first structural element is configured for mating engagement with a complimentary recess in the second structural element.

18. The implant according to claim 1, wherein the first and second structural elements are coupled by interlocking.

19. The implant according to claim 1, wherein the first and second structural elements are coplanar whelk coupled by engaging one or more recesses.

20. The implant according to claim 1, wherein one or more recesses extend from the first end of the first structural element and one or more recesses extend from the second end of the second structural element that is coupled to the first structural element.

21. A method of fusing one or more bones, comprising:
providing a first and a second structural element, wherein each structural element includes a first end spaced apart from a second end by an inner side surface and an outer side surface; and one or more notches extending only partially from one end of each structural element and extending fully from the outer side surface to the inner side surface of each structural element;
engaging one or more recesses of the first structural element with one or more recesses of the second structural element to form a modular implant; and
inserting the modular implant adapted for implantation between first and second adjacent vertebral bodies between the bones, wherein, when implanted, the first end of each of the first and second structural elements engages one of the first vertebral bodies and the second end of each of the first and second structural elements engages the other of the first and the second vertebral bodies.

22. A method of fusing one of more bones, comprising:
providing a first, second and third structural element, wherein each structural element includes a first end spaced apart from a second end by a side surface; and one or more notches in the side surfaces extending from the first end;
engaging one or more notches of the first structural element with one or more notches of the second and third structural elements to form a modular implant; and
inserting the modular implant adapted for implantation between first and second adjacent vertebral bodies between the bones, wherein, when implanted, the first end of each of the first, second and third structural elements engages one of the first and second vertebral bodies and the second end of each of the first, second and third structural elements engages the other one of the first and second vertebral body.

23. A method for manufacturing a modular implant for implantation between first and second adjacent vertebral bodies, the method comprising:
cutting one or more structural elements from a segment of bone, wherein the structural elements each include first and second ends spaced apart by an inner side surface and an outer side surface;
forming one or more recesses in the side surfaces, wherein forming the recesses involves creating notches extending only partially from one end of each structural element and extending fully from the outer side surface to the inner side surface of each structural element, and
coupling two or more structural elements by engaging the recesses of one structural element with the recesses of another structural element, wherein, when implanted, the first end of each structural element is adapted to engage one of the first and second vertebral bodies and the second end of each structural element is adapted to engage the other one of the first and the second vertebral bodies.

24. The method of claim 23, wherein cutting the structural elements from a segment of bone involves forming the elements such that they have a shape in cross-section that is rounded.

25. A modular implant comprising:
a first end and a second end;
a body extending from the first end to the second end,
structural elements adapted to interlock in more than one orientation to form the body,
wherein the structural elements are adapted such that a same set of structural elements can both form a body of the implant that is curved, wherein each structural element is adjacent to no more than two other structural elements and a line connecting longitudinal axes of the structural elements is curved, if the structural elements are interlocked in a first orientation and form a body of the implant that is linear, wherein each structural element is adjacent to no more than two other structural elements and a line connecting longitudinal axes of the structural elements is generally linear, if the structural elements are interlocked in a second orientation.

26. A modular implant for implantation between first and second adjacent vertebral bodies, the implant comprising:
a first and a second structural element, each including
a first end spaced apart from a second end by a side surface; and
one or more recesses in the side surface,
wherein in each structural element the first end is spaced apart from the second end by an inner side surface and an outer side surface, the recesses extending only partially from one end of each structural element and extending fully from the outer side surface to the inner side surface of each structural element and wherein the first and second structural elements are coupled by engaging one or more recesses and wherein, when implanted, the first end of each of the first and second structural elements engages one of the first and second vertebral bodies and the second end of each of the first and second structural elements engages the other one of the first and second vertebral bodies.

* * * * *

UNITED STATES PATENT AND TRADEMARK OFFICE
CERTIFICATE OF CORRECTION

PATENT NO. : 7,037,339 B2
APPLICATION NO. : 10/261081
DATED : May 2, 2006
INVENTOR(S) : Rodney L. Houfburg It is certified that error appears in the above-identified patent and that said Letters Patent is hereby corrected as shown below:

Column 5, line 22, change "(see, for example, FIG. 1B)" to --(see, for example, FIG. 1B).--.

Column 7, line 16, change "II. Modular Implant" to --III. Modular Implant--.

Column 8, line 38, change "including linear and curves sections" to --including linear and curved sections--.

Column 9, line 6, change "the modular implant includes or a radius of curvature" to --the modular implant includes a radius of curvature--.

Column 9, line 22, change "the width the of the load-bearing surface" to --the width of the load-bearing surface--.

Column 9, line 54, change "one another structural element 1." to --one other structural element 1.--.

Column 10, line 36, change "III. Method" to --IV. Method--.

Column 10, line 64, change "IV. Inserter Tool" to --V. Inserter Tool--.

Column 11, line 67, change "extending fully from the outer side surface to the inner side surface, of each structural element" to --extending fully from the outer side surface to the inner side surface of each structural element,--, as amended in the Notice of Allowance by Examiner on Page 2.

Column 12, line 64, change "engagement with a complimentary recess" to --engagement with a complementary recess--.

Column 13, line 2, change "whelk" to --when--, as shown in the Amendment dated December 15, 2003, on page 9, new claim 27, now claim 19.

UNITED STATES PATENT AND TRADEMARK OFFICE
CERTIFICATE OF CORRECTION

PATENT NO. : 7,037,339 B2
APPLICATION NO. : 10/261081
DATED : May 2, 2006
INVENTOR(S) : Rodney L. Houfburg It is certified that error appears in the above-identified patent and that said Letters Patent is hereby corrected as shown below:

Column 14, line 3, change "of each structural element," to --of each structural element;--, as shown in the Amendent and Response dated September 9, 2005, on page 4, claim 18, now claim 23.

Signed and Sealed this

Fourteenth Day of November, 2006

JON W. DUDAS
*Director of the United States Patent and Trademark Office*